United States Patent [19]

Thompson

[11] Patent Number: 5,391,193
[45] Date of Patent: Feb. 21, 1995

[54] METHOD AND APPARATUS FOR BATTERY DEPLETION MONITORING

[75] Inventor: David L. Thompson, Fridley, Minn.

[73] Assignee: Medtronic, Inc., Minneapolis, Minn.

[21] Appl. No.: 14,296

[22] Filed: Feb. 5, 1993

[51] Int. Cl.⁶ .............................................. A61N 1/08
[52] U.S. Cl. ...................................... 607/29; 324/430
[58] Field of Search ............................. 607/29, 27, 32; 324/430

[56] References Cited

U.S. PATENT DOCUMENTS

| | | | |
|---|---|---|---|
| 4,231,027 | 10/1980 | Mann et al. | 340/636 |
| 4,259,639 | 3/1981 | Renirie | 324/430 |
| 4,324,251 | 4/1982 | Mann | 128/419 |
| 4,715,381 | 12/1987 | Moberg | 607/29 |
| 5,137,020 | 8/1992 | Wayne et al. | 128/419 |

OTHER PUBLICATIONS

Datakey Data Sheet for Model DK1400 Data Key.
Datakey Preliminary Data Sheet for Model DT 1402 Data Tag and Model TRSR1402L Tag Receptacle.

Primary Examiner—William E. Kamm
Assistant Examiner—Kennedy J. Schaetzle
Attorney, Agent, or Firm—Harold R. Patton

[57] ABSTRACT

A method and apparatus for estimating the remaining capacity of a lithium-iodine battery through the nomographic analysis of two or more measurements of battery impedance. In a preferred embodiment, a pacemaker or other implantable medical device is provided with circuitry for periodically measuring the internal impedance of its battery. Each measurement of impedance is stored along with an indication of when such measurement was made. Nomographic analysis, based upon the rated capacity of the battery and the expected internal impedance at various stages of depletion, allows for two or more time-stamped impedance measurements to serve as the basis for an extrapolation to estimate the remaining service life of the implantable medical device. Nomographic analysis may be performed by circuitry contained in the implanted device itself; in the alternative, periodic impedance measurements may be communicated to external processing circuitry via a telemetry channel.

11 Claims, 3 Drawing Sheets

METHOD AND APPARATUS FOR BATTERY DEPLETION MONITORING

FIELD OF THE INVENTION

This invention relates to the field of implantable medical devices, and more particularly relates to circuits for determining the depth of discharge of lithium-iodine batteries in a pacemaker or other battery-powered medical device.

BACKGROUND OF THE INVENTION

The number of patients with implanted pacemakers, cardioverters, defibrillators, neural stimulators, and the like is steadily increasing around the world, and is likely to continue to do so. A great many of these patients are partially or completely dependent upon their implanted devices, and it is very important for implanted devices to operate reliably. It has always been desirable for a clinician to be able to readily obtain reliable information about various aspects of an implanted device's operational status. The status of the device's power supply is of particular concern.

The most prevalent source of power used in implanted devices is battery power, very often from lithium-iodine cells. Many systems have been proposed in the prior art for providing some sort of battery end-of-life (EOL) indication when the device's power supply is nearly depleted. Of course, it is desirable for the circuitry for generating the EOL indication to be able to anticipate battery depletion early enough to allow time for appropriate remedial action to be taken, such as replacement of the device.

With the advent of improved batteries which can last for many years before depletion, the need has arisen for more information than a simple EOL indication. For example, it has been deemed desirable for the device to provide information regarding how much longer the battery will last under the normal demand that is placed on it.

Lithium-iodine batteries have a characteristic feature that their internal resistance curve is substantially linear as a function of energy depletion until near EOL, at which time the curve exhibits a "knee" where internal resistance begins to rise rapidly. In lithium-iodine batteries, the cell cathode consists of molecular iodine weakly bonded to polyvinyl pyridine (P2VP). The initial cathode composition of lithium-iodine batteries is often expressed as the weight ratio of $I_2$ to P2 VP. Typical values of this ratio range from 20:1 to 50:1. No electrolyte as such is included in the construction of the cell, but a lithium iodine (LiI) electrolyte layer forms during cell discharge, between the anode and the cathode. The LiI layer presents an effective internal resistance to Li+ ions which travel through it. Since the LiI layer grows with the charge drawn from the battery, this component of the battery resistance increases linearly as a function of energy depletion. In the implantable device context, where there is typically a relatively continuous energy depletion, this component of the internal resistance increases continually over time. However, particularly for a demand type pacemaker which at any given time may or may not be called upon to deliver stimulating pulses, the increase in this component is continuous but not necessarily linear with time, due to the fact that current drain is not constant.

Another component of internal resistance in lithium-iodine cells is caused by depletion of iodine in the cathode. The cathode is essentially a charge transfer complex of iodine and P2VP, and during discharge of the cell iodine is extracted from this complex. As noted above, the weight ratio of $I_2$ to P2VP at beginning of life may range from 20:1 to 50:1. During extraction of iodine from the complex, the resistance to this process is low until the point is reached where the $I_2$-to-P2VP ratio is reduced to approximately 8:1, the ratio at which the cathode becomes a single phase and the iodine activity begins to be less than unity. At this point the resistance rises sharply. This gives rise to a non-linear internal resistance component which, for the lithium-iodine cell, is called variously the depletion resistance, depolarizer resistance, the charge-transfer complex resistance, or the pyridine resistance. By whatever names, the combination of the non-linear component with the linear component produces an overall resistance curve with a knee occurring toward EOL, the knee being caused by the reaching of the depletion of available charge carriers from the cathode.

In the prior art, some EOL indicator arrangements in implantable devices evaluate battery life based simply upon the terminal voltage of the battery, indicating EOL when the voltage falls below a predetermined threshold. However, due to the internal impedance of the battery, terminal voltage varies significantly depending upon current consumption. Thus, if relatively little current is drawn from the battery for a period of time when the battery is nearing but has not reached its EOL, a sudden prolonged period of high demand on the battery may cause a situation in which too little time is available between indication of EOL and total depletion of the battery. For a particular pacemaker and electrode combination in a given patient, there will be a variation in the effective load on the lithium-iodine battery, and a resulting variation in the overall current drain. Accordingly, if an EOL indication is predicated upon sensing the voltage of the battery and detecting when it drops below a certain level, there can be very little assurance that the level chosen will correspond to the knee of the internal resistance curve.

It has been recognized in the prior art that since remaining battery life is directly related to the internal impedance of the battery itself, remaining battery life can be reliably predicted through accurate measurement of internal battery impedance. In U.S. Pat. No. 5,137,020 issued to Wayne et al. and assigned to the assignee of the present invention, there is described a battery impedance measuring arrangement wherein a current source and a reference impedance are applied to a battery which has been isolated from the remainder of the pacemaker circuitry. The Wayne et al. '020 patent is hereby incorporated by reference in its entirety into the present disclosure.

Other battery impedance measuring arrangements are proposed, for example, in U.S. Pat. Nos. 4,259,639 to Renirie, 4,231,027 to Mann et al., and 4,324,251 to Mann. These patents are also hereby incorporated by reference herein in their entirety. The theory underlying the use of internal impedance as a EOL warning indicator is that at low current drains typical of implantable medical devices, plots of resistance versus time give more warning than plots of terminal voltage over time. If voltage characteristics for different current drains are considered, the knees in the impedance curve are observed to have a fairly wide variation, meaning that the voltage at which the knee might appear is similarly subject to substantial variation as a function not only of the particular battery being used but also of the current being drawn by the pacemaker circuitry at a given time. On the other hand, plots of resistance indicate that the knee varies over a smaller range of values of internal resistance. Since the current drain may vary drastically with different electrode loads, the variation in voltage may be many times the variation in internal resistance. Monitoring the internal resistance thus provides a more direct indication of the depth of discharge of the battery, whereas monitoring the output voltage gives a much less direct indication, reflecting not only the depth of discharge but also the current drain.

Although the internal impedance of an implanted battery is believed to more accurately reflect the level of battery depletion than the battery voltage, errors still exist. For example, open circuit battery voltage typically changes by 28-mV or so from beginning-of-life (BOL) to end-of-life. This leads to a typical 5% error in an expected 20-kΩ end-of-life impedance level. It is one feature of the present invention, therefore, that such variation in open-circuit battery voltage is accounted for in the computation of a battery's internal resistance.

SUMMARY OF THE INVENTION

In accordance with the present invention, a method and apparatus for determining the expected longevity of an implanted battery utilizes readings of a battery's current drain and open circuit voltage taken at various times during the operational life of the battery. Each time readings of battery voltage and current drain are made, two values are computed: the length of time from implant (the "time-from-implant"value) and the present value of the battery's internal impedance ($R_{DC}$). All values of battery impedance and time-from-implant are stored as pairs for future use, for example in memory within the implantable device, or in an external programming device communicating with the implantable device via a telemetry link.

Further in accordance with the present invention, each time measurements of battery voltage and current drain are made, the time-from-implant/internal impedance data pairs reflecting the operational life of the battery from time-of-implant to present are subjected to nomographic analysis, providing a means for the extrapolation of the expected longevity of the battery. The nomographic extrapolation of the expected longevity may be made based upon the initial data point and the current data point, or based upon a curve which is fitted to the most recent two or three data points or alternatively, to all the available data points. In this way, the above-noted variations in computed battery impedance resulting from variations in current drain on the battery are averaged out during the successive computations of longevity. That is, the method and apparatus of the present invention are less sensitive to variations in localized data points.

It is an additional feature of the present invention battery impedance measurements are made and recorded throughout the operational lifetime of the battery, and that because all new data is utilized in conjunction with previously obtained data, the nomographically projected battery longevity becomes increasingly reliable and accurate throughout the battery's life.

While nomographic analysis provides the theoretical basis for obtaining an estimate of time of battery depletion in accordance with the present invention, it is one feature of the present invention that an actual nomographic representation of the data points may not actually be generated. Instead, it is believed to be preferable for the nomograph to actually be expressed in the form of a set of mathematical relations, or as an organized set of tables of values, so that the nomographic analysis can be performed as a series of mathematical steps or as a succession of table look-ups. In this way, the nomographic extrapolation of battery longevity may be readily performed by a digital computer or other electronic processing circuitry.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
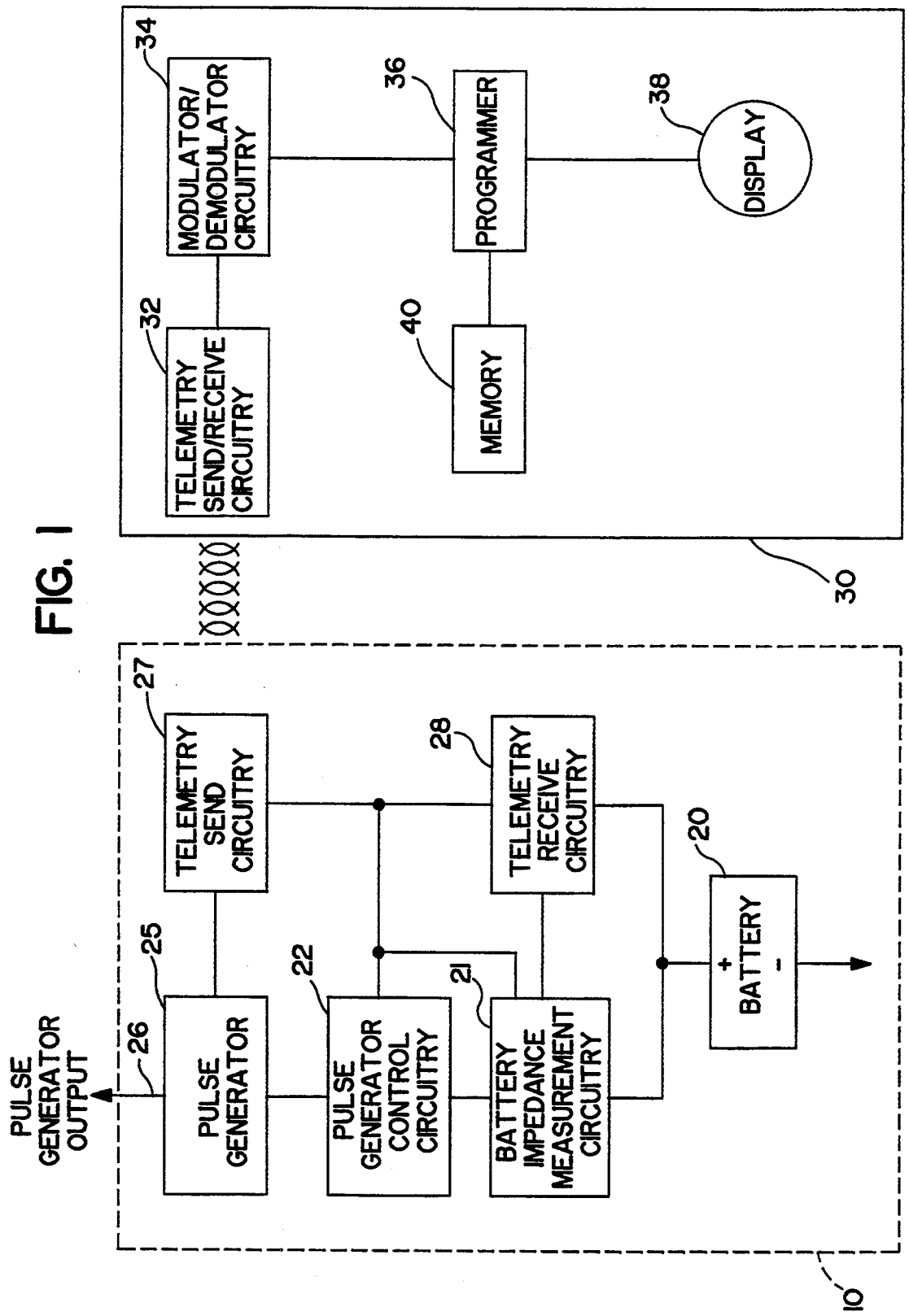
FIG. 1 is a block diagram of an implantable medical apparatus in accordance with one embodiment of the invention.

FIG. 1 is a simplified block diagram of an implantable medical apparatus for which the present invention is believed to be especially advantageous. A battery operated, body-implantable medical device 10 is shown generally within dotted lines in FIG. 1, the dotted lines being indicative of the implantation of medical device 10 within a patient's body. Medical device 10 may be any one of a number of implantable medical/electrical circuits, such as the Medtronic Elite ™ or Medtronic Legend ™, for example, the latter being described in U.S. Pat. No. 5,052,388 to Sivula et al., which patent is hereby incorporated by reference herein in its entirety. Medical device 10 is shown in FIG. 1 to include a pulse generator, for example, of the type used in the Sivula et al. pacemaker.

Medical device 10 in FIG. 1 is shown to further include a telemetry capability for communicating with a telemetry controller 30. The use of telemetry with implantable medical devices for controlling and reading signals from and to the implanted apparatus is now believed to be so well known in the art that no further general explanation is needed; see, for example, U.S. Pat. No. 4,231,027. A telemetry system suitable for use in the practice of the present invention is disclosed in U.S. Pat. No. 4,556,063 issued to Thompson et al. on Dec. 3, 1985 and entitled "Telemetry System for a Medical Device", which patent is hereby incorporated by reference herein in its entirety.

With continued reference to FIG. 1, implanted medical device 10 is shown to include a battery 20 connected to provide power to other elements of device 10. Medical device 10 also includes battery impedance measurement circuitry 21, pulse generator control circuitry 22, pulse generator 25 having an output 26, telemetry transmitter circuitry 27 and receiver circuitry 28. Each of these elements of medical device 10 shown in FIG. 1 are well known to those of ordinary skill in the art, and will not be further described herein in detail. An impedance measurement circuit suitable for the purposes of the present invention is disclosed in the above-referenced U.S. Pat. No. 5,137,020 to Wayne et al. Other impedance measurement circuits are also known in the art and believed to be suitable for the purposes of the present invention; see, for example, U.S. Pat. No. 4,606,350 to Frost.

Telemetry controller 30 includes telemetry transmit and receive circuitry 32, modulate/demodulate circuitry 34, programmer 36, and display means 38. Programmer 36 is, in the presently preferred embodiment of the invention, an IBM PC-compatible computer system having numeric processing capabilities which may be utilized in the practice of the present invention, as shall hereinafter be described in greater detail. In particular, it is believed that programmer 36 may be configured to perform the numeric computations necessary for linear or curve-fitting estimation of battery longevity in accordance with the presently disclosed embodiment of the invention.

As is commonly practiced in the art, programmer 36 can be controlled by an operator to send a plurality of signals to medical device 10 that comprise, for example, a set of operational parameters for the output of pulse generator 25. The signals from programmer 36 are modulated by circuitry 34 and telemetered by telemetry transmit and receive circuitry 32 to medical device 10. Telemetry receive circuitry 28 will receive and demodulate the signals and present them to pulse generator control circuitry 22 which will use the signals to set the parameters for pulse generator 25. Telemetry transmit circuitry 27 in medical device 10 may be used, for example, to monitor the operation of pulse generator 25 and other components of device 10, and to modulate and send the information to telemetry transmit and receive circuitry 32 of telemetry controller 30. The information is then demodulated in modulate/demodulate circuitry 34 and presented to programmer 36, and thence to display means 38 for review by the operator, or to be used by programmer 36 as the basis of additional computations, or may be stored in memory 40 for later use.

Programmer 36 may be selectively actuated to send a signal through the telemetry channel described above to activate battery impedance measurement circuitry 21. When this signal is received, battery impedance measurement circuitry 21 will measure the internal impedance of battery 20 at that point in time, in a manner fully described the above-referenced Wayne et al. '20 patent. When the desired measurement is completed, battery impedance measurement circuitry 21 provides a signal containing the measurement value through the telemetry path to telemetry controller 30 to be received by programmer 36. In addition, the measurement value provided by measurement circuit 21 may be stored in memory within device 10 itself (such memory not being shown in FIG. 1). As would be appreciated by those of ordinary skill in the art, device 10 may further include processing circuitry (not shown in FIG. 1), for example a microprocessor system or the like, which may perform the numeric calculations in accordance with the presently disclosed embodiment of the invention, without the necessity of telemetering out the impedance value to programmer 36. In this case, the computed value of projected battery longevity can be telemetered to programmer 36 for display on display means 38.

When a measurement of battery impedance is provided by measurement circuit 21, a value reflecting the time at which such measurement was made is also produced. In the presently preferred embodiment of the invention, the time of interest is the "time-from-implant" and may be expressed in terms of months. This time value may be provided from an internal "real-time" clock (not shown) included within the circuitry of device 10, or alternatively may be provided by the operator of telemetry controller, either to be used by processing circuitry within controller 30 (in the case where the projected longevity computation in accordance with the present invention is made in telemetry controller 30), or to be telemetered to device 10 to be used by processing circuitry therein (in the case where the projected longevity computation is performed within device 10 itself).

In either case, each measurement of battery impedance is associated with a particular time value indicating when such measurement was made; thus, at various times during the life of the battery, a time-from-implant/internal impedance data pair is produced; such data pairs are stored either in memory in the device itself or in memory 40 associated with telemetry controller 30. Alternatively, memory 40 may be a removable memory element such as a data tag or data key from Datakey Inc.

Figure 2:
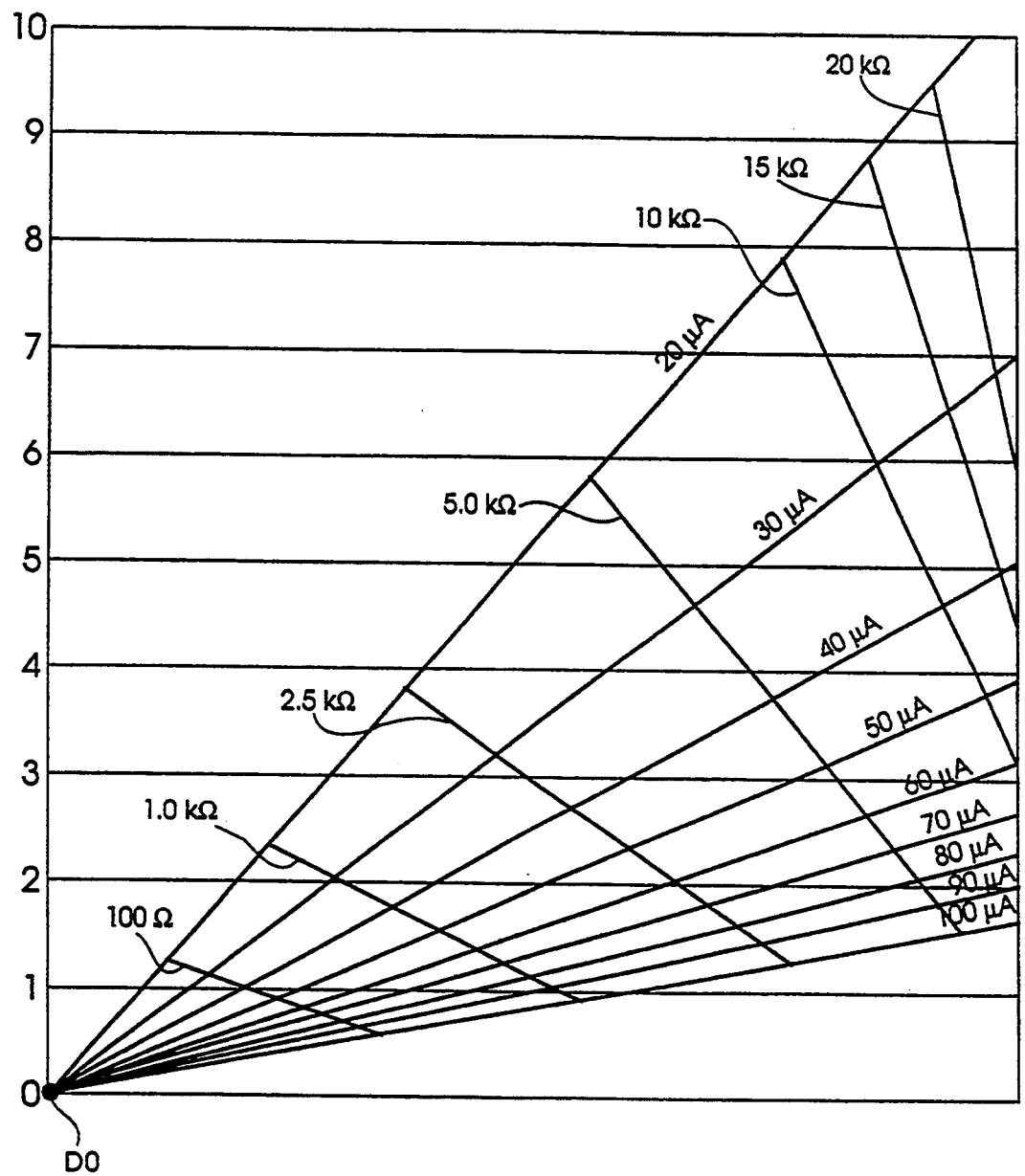
FIG. 2 is a nomograph used for longevity extrapolation in accordance with one embodiment of the invention.

Turning now to FIG. 2, there is shown a nomograph in accordance with the presently disclosed embodiment of the invention. As used herein, and as would be appreciated by those of ordinary skill in the art, the term "nomograph" will refer to a graphical representation consisting of several lines marked off to scale and arranged in such a way that by connecting known values on two lines, either with a straight line or with a fitted curve, an unknown value can be read at the point of intersection of another line. As will hereinafter be explained in greater detail, the nomograph of FIG. 2 enables a battery impedance measurement value taken at a particular time (i.e., a time-from-implant/internal impedance data pair) to be used as a basis for predicting the remaining longevity of a battery. Additionally, as additional battery impedance measurements are made at subsequent times, these new measurements may be used in conjunction with previous measurements to minimize the impact of the above-discussed temporary current drain variations and other time-localized variations in measured impedance on longevity estimates. That is, as more and more impedance data is obtained over a period of time, the longevity estimate obtained in accordance with the present invention becomes increasingly reliable and accurate.

The nomograph of FIG. 2 has units of zero through ten years along its vertical axis. The nomograph further consists of a series of "constant current drain" lines, designated as 20-$\mu$A, 30-$\mu$A ... 100-"A in FIG. 2. These constant current lines originate at the origin (point DO in FIG. 2), at time T=0(i.e., the time of implant), and extend to the right side of the nomograph. The constant current lines reflect the rated capacity of a given battery type, which is typically expressed in units of milliamp-hours. The 30-$\mu$A constant current drain line, for example, corresponds to the battery being subjected to a 30-$\mu$A current drain throughout its lifetime. The 30-$\mu$A constant current drain line intersects the right side of the nomograph in FIG. 2 at approximately the seven year level; this means that for the battery capacity represented in the nomograph of FIG. 2, a battery subjected to a continuous 30-$\mu$A current drain will be depleted in approximately seven years.

The nomograph of FIG. 2 also includes a plurality of impedance curves, designated 2.5-k$\Omega$5.0-k$\Omega$, ... 20-k$\Omega$. Each impedance curve intersects each constant current drain line. Where an impedance curve intersects a given constant current drain line, the value of the impedance curve (i.e., 2.5-kΩ, 5.0-kΩ, etc . . .) is the expected internal impedance at that time of a battery being drained at the given constant current. As would be appreciated by those of ordinary skill in the art, the arrangement of impedance lines in the nomograph will be unique to each type of battery. Furthermore, although the impedance curves in FIG. 2 are shown as being substantially straight, it is to be understood that this is merely an approximation of the expected impedance at various current drains based on the assumption that the battery's impedance build-up is a linear function of current drain. In fact, the impedance curves may be curvilinear; however, the straight-line approximation of impedance curves FIG. 2 is believed to be sufficient for the purposes of practicing the present invention.

After an impedance measurement has been obtained, the first step in using the nomograph of FIG. 2 is to locate the intersection of a horizontal line corresponding to the time-from-implant at which an impedance measurement is made, with the impedance curve corresponding to that measured impedance. Although only a few impedance curves have been shown in Figure 2, it is to be understood that many more may be provided. A line drawn from the initial implant data point through this intersection point can be extended to the right edge of the nomograph of FIG. 2 to yield an extrapolated battery depletion time.

In the alternative, after a period of time during which multiple impedance/time-from-implant data pairs have been obtained and stored, the data points corresponding to each of the pairs can be supplied to a curve-fitting algorithm to generate a curve from which end of battery life may be extrapolated on the nomograph of FIG. 2.

The nomograph of FIG. 2 is based on certain underlying assumptions. In particular, it is assumed for the nomograph of FIG. 2 that the battery has an initial open-circuit voltage of 2.8 -volts and an end-of-life open-circuit voltage of 2.15 -volts. It has been the inventor's experience that such values are typical of batteries in implantable pacemakers and the like.

Figure 3:
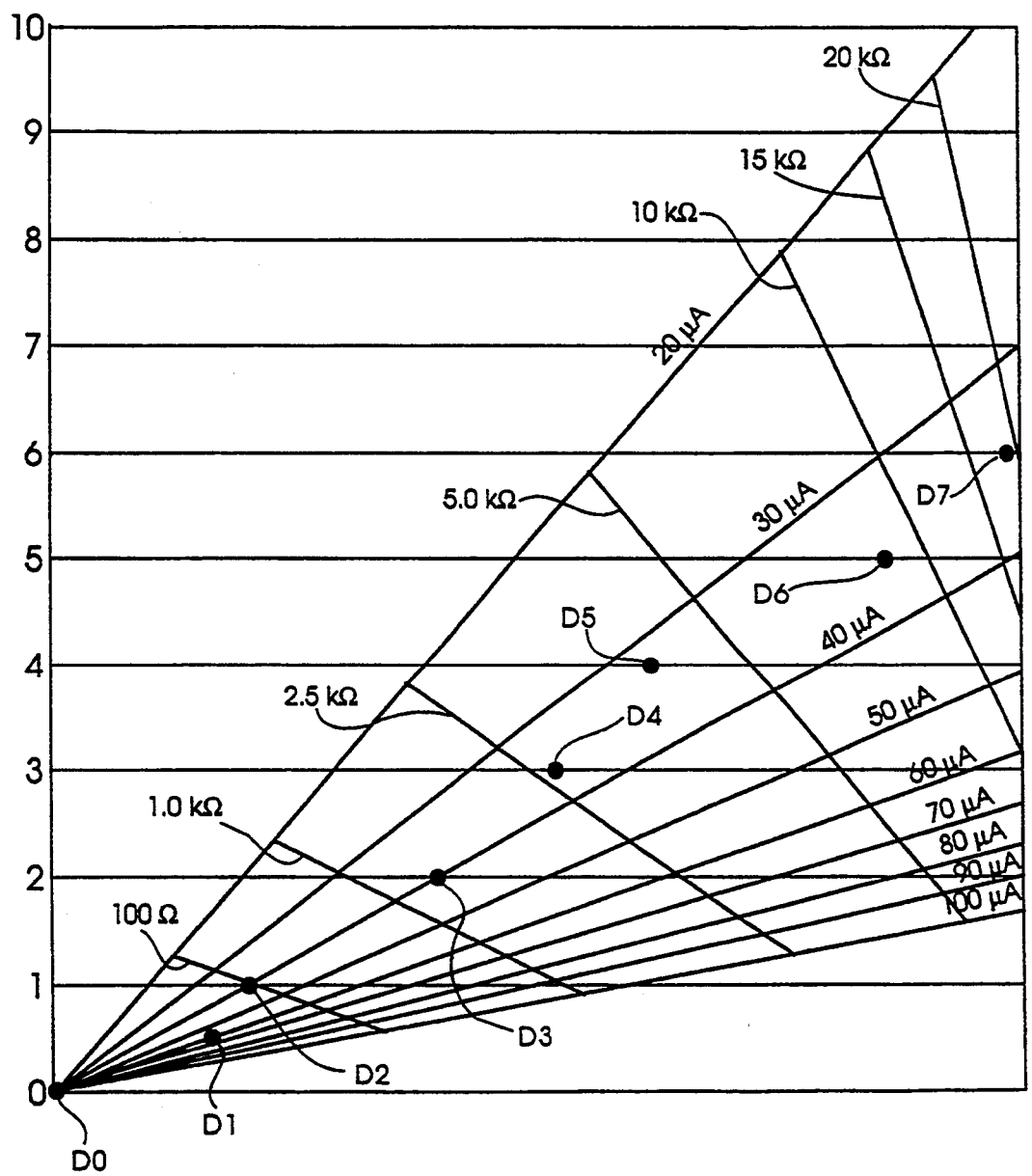
FIG. 3 is the nomograph from FIG. 2 having several data points plotted thereon.

The use of the nomograph in accordance with the presently disclosed embodiment of the invention may perhaps best be understood with reference to the following particular example: In FIG. 3, there is shown the nomograph of FIG. 2 having a number of data points plotted thereon. A first data point, D1 in FIG. 3, corresponds to a 50 -Ω measured data impedance of a battery at one-half of a year after implant. Likewise, a second data point, D2, corresponds to a 100 Ω impedance at 1 year after implant, a third, D3, corresponds to approximately a 1.5 -kΩ impedance measured at 2 years after implant, and so on.

Each time a new impedance measurement is made, an updated estimate of battery longevity can be nomographically extrapolated from the nomograph of FIG. 3. At one-half year after implant, for example, when data point D1 is obtained, a straight line through the starting point (D0) and the data point D1 can be extended to the right side of the nomograph to yield an extrapolated longevity estimate of just over three years.

At one year after implant, a second impedance reading, plotted as D2 in FIG. 3, is made. If a line is drawn through points D0 and D2 and extended to the right side of the nomograph, this yields a new longevity estimate of approximately five years.

At two years after implant, a third impedance reading, plotted as D3 in FIG. 3, is made. A line drawn through points D0 and D3 and extended to the right side again yields a longevity estimate of approximately five years. Alternatively, a curve fitting algorithm could be used to project a longevity estimate utilizing points D0, D1, D2, and D3.

In the foregoing description, it has been assumed that the computation of longevity estimates is performed nomographically using the nomograph of FIGS. 2 and 3. In actual implementation, however, it is believed to be preferable to express the nomograph as a collection of look-up tables or as a set of mathematical relations. A separate table of values would be provided for each of a plurality of impedance curves. In the example nomograph shown in Figures 2 and 3, a separate table of values would be provided for each of the 100-Ω, 1.0-kΩ, 2.5-kΩ, ... 20-kΩ impedance curves. A measured impedance value would be used to select one of the impedance curve tables. From the selected impedance curve table, a particular entry in that table will be selected based upon the time-from-implant of the measurement of impedance. The entry may consist, for example, of an (x,y) coordinate pair defining a single point in the nomograph. This coordinate pair, along with the coordinates of the origin (0,0), can be used to define a straight line of a particular slope. Then, it is a simple matter to determine where such line would intersect the right-hand side of the nomograph; the vertical coordinate of this intersection point would identify the estimated longevity.

The expression of a nomograph such as is shown in FIGS. 2 and 3 in the form of tables or mathematical expressions can be accomplished in various suitable ways, and it is believed that it would be a matter of routine for those of ordinary skill in mathematics to do so.

If more than the present data and the time-of-implant data are to be considered in the nomographic extrapolation, a curve-fitting algorithm may be used to determine the equation for a curve which contains the points to be considered. One curve-fitting algorithm believed to be suitable for the purposes of the present invention is disclosed in Johnson, "Multidimensional Curve Fitting Program for Biological Data ", Computer Programs in Biomedicine 18 (1984) 259–264, which is hereby incorporated by reference in its entirety. The algorithm disclosed in the Johnson reference is implementable in the IBM PC-compatible system of programmer 36. Thus, in one embodiment of the invention, the impedance data from pacemaker 10 is telemetered to telemetry controller and provided to programmer 36.

Programmer 36, configured to perform linear or curve-fitting extrapolation based on the impedance data collected, can thus derive an equation fitted to the data. Once such an equation has been obtained, it is again a simple mathematical step to determine the point of intersection of that curve with the right-hand side of the nomograph. Although the Johnson reference has been specifically identified herein, it is believed that various known curve-fitting algorithms implementable in the processing circuitry of the implantable device or external telemetry controller would be suitable for the purposes of the present invention.

Alternatively, it is contemplated that the collection of look-up tables corresponding to a given nomograph could be contained in memory within the implanted device itself, to be accessed by numeric processing circuitry within the device, or that the tables may reside in the telemetry controller 30, to be accessed after measured impedance values are telemetered out of the device.

From the foregoing detailed description of specific embodiments of the invention, it should be apparent that a method and apparatus for estimating the remaining longevity of a battery in an implanted medical device has been disclosed. Although a particular method and apparatus have been disclosed herein in some detail, this has been done for the purposes of illustration only, and is not intended to be limiting with respect to the scope of the invention as defined in the appended claims. It is contemplated that various alterations, substitutions, and modifications to the disclosed method and apparatus may be made without departing from the spirit and scope of the invention as defined in the following claims.

What is claimed is:

1. A method for metering remaining longevity of an implantable medical device battery, comprising the steps of:
   (a) generating a first signal having a first value corresponding to a measured internal impedance of said battery;
   (b) generating a second signal having a second value corresponding to time-from-implant of said measured internal impedance;
   (c) defining a nomograph having a plurality of time lines, impedance curves, and constant current-drain lines therein, said nomograph relating each one of said plurality of constant current lines to an estimate of battery longevity;
   (d) locating in said nomograph an impedance curve corresponding to said first value;
   (e) locating in said nomograph an intersection point between said corresponding impedance curve and a time line corresponding to said second value;
   (f) repeating steps (a), (b), (d) and (e) at least once to locate a plurality of said intersection points;
   (g) nomographically extrapolating an estimate of battery longevity based upon said plurality of intersection points; and
   (h) generating a third signal having a third value corresponding to said longevity estimation.

2. A pacemaker system, comprising:
   an implantable housing containing a battery means for powering said pacemaker;
   a battery impedance measurement circuit means for generating impedance signals corresponding to measured impedances of said battery;
   a transmitting means for transmitting said impedance signals; and
   a telemetry unit means for receiving said impedance signals, wherein said telemetry unit further comprises means for generating time values indicating when said impedance signals were generated, and means for calculating estimated battery longevity based upon said impedance signals and said time values.

3. A system according to claim 2, wherein said telemetry unit further comprises a display means for displaying said estimated battery longevity.

4. A system according to claim 2 or claim 3, wherein said telemetry unit further comprises a memory means for storing said impedance signals and said time values.

5. A system according to claim 4, wherein said memory means is removable from said telemetry unit.

6. A system according to claim 2 or claim 3, wherein said telemetry unit further comprises means for transmitting command signals to said implantable device and wherein said implantable device further comprises means responsive to said command signals for triggering said battery impedance measurement circuit means to generate impedance signals.

7. A system according to claim 2 or claim 3, wherein said means for generating time values comprises means for generating time values indicative of times elapsed since implant of said implantable device.

8. A system for determining longevity of an implantable device battery, comprising:
   an implantable device housing containing a battery;
   an impedance measurement circuit for generating impedance signals corresponding to measured impedances of said battery;
   means for generating time values corresponding to times of generation of said impedance signals; and
   means for calculating estimated battery longevity based upon said impedance signals and said time values.

9. A system according to claim 8, further comprising a display means for displaying said estimated battery longevity.

10. A system according to claim 8 or claim 9, wherein said system further comprises a memory means for storing said impedance signals and said time values.

11. A system according to claim 8 or claim 9, wherein said means for generating time values comprises means for generating time values indicative of times elapsed since implant of said implatable device.

* * * * *